(12) United States Patent
Holladay

(10) Patent No.: US 7,324,846 B2
(45) Date of Patent: *Jan. 29, 2008

(54) METHOD OF ENCHANCING ELECTRONTRANSPORT POLYPEPTIDE FLUX BY AMINO ACID SUBSTITUTION WITH HISTIDINE

(75) Inventor: Leslie A. Holladay, Mountain View, CA (US)

(73) Assignee: Alza Corp., Mountain View, CA (US)

( * ) Notice: Subject to any disclaimer, the term of this patent is extended or adjusted under 35 U.S.C. 154(b) by 944 days.

This patent is subject to a terminal disclaimer.

(21) Appl. No.: 10/016,403

(22) Filed: Dec. 10, 2001

(65) Prior Publication Data

US 2002/0107505 A1 Aug. 8, 2002

Related U.S. Application Data

(63) Continuation of application No. 08/466,610, filed on Jun. 6, 1995.

(51) Int. Cl.
 A61N 1/30 (2006.01)
 A61K 38/00 (2006.01)
(52) U.S. Cl. .............................. 604/20; 514/2; 530/324
(58) Field of Classification Search .................. 514/2; 604/20
 See application file for complete search history.

(56) References Cited

U.S. PATENT DOCUMENTS

| | | | | |
|---|---|---|---|---|
| 4,250,878 | A | 2/1981 | Jacobsen et al. | 128/207.21 |
| 4,383,529 | A | 5/1983 | Webster | 604/20 |
| 4,431,739 | A | 2/1984 | Riggs | 435/253 |
| 4,528,190 | A * | 7/1985 | Vale et al. | 514/12 |
| 4,628,043 | A | 12/1986 | Spiess et al. | 514/12 |
| 4,631,211 | A | 12/1986 | Houghten | 428/35 |
| 4,722,726 | A | 2/1988 | Sanderson et al. | 604/20 |
| 5,013,653 | A | 5/1991 | Huston et al. | 435/69.7 |
| 5,250,022 | A | 10/1993 | Chien et al. | 604/20 |
| 5,250,023 | A | 10/1993 | Lee et al. | 604/20 |
| 5,494,679 | A | 2/1996 | Sage, Jr. et al. | 424/443 |

FOREIGN PATENT DOCUMENTS

| | | |
|---|---|---|
| EP | 0 278 473 | 8/1988 |
| EP | 0 643 981 | 9/1994 |
| EP | 0 667 355 | 2/1995 |
| WO | WO 92/12999 | 8/1992 |
| WO | WO 93/25197 | 12/1993 |
| WO | WO 95/11988 | 5/1995 |

OTHER PUBLICATIONS

Steadman et al. (1998) Biochemstry 37:7089-7095.*
"Introduction to Protein Structure," Branden and Tooze, Garland Publishing, Inc., New York, 1991, p. 247.*
Colman et al. Res Immun 145:33-36, 1996.*
Abaza et al. J Protein Chem 11:433-444, 1992.*
Hoppe-Seyler's Z. Physiol Chem (1979) 360:1619-1632.*
Voet et al., "Biochemistry," John Wiley and Sons, New York, 1990, pp. 61-64.*
Kumar et al. (1990) Proc Intern Symp Control Rel Bioact Mater 17:435-436, Controlled Release Society, Inc.*
Obermuller et al. (2002) J Cell Sci 115:185-194.*
Burnette, et al., *J. Pharm. Sci.*, (1986) vol. 75, 738.
Chien, et al., *J. Pharm. Sci.*, (1988) vol. 78, 376.
Maulding, et al., U.S. Statutory Invention Registration No. H1160, 1993.
Nozaki, et al., *J. Biol. Chem.*, (1971) vol. 246, 2211-2217.
Merrifield, et al., *Biochemistry*, (1981) vol. 21, 5020.
Bodanszky, "Principles of Peptide Synthesis," (1984) Akad.-Verlag.
Stewart, et al., "Solid Phase Peptide Synthesis," (1969) Freeman.
Houghten, *Proc. Natl. Acad. Sci. USA*, (1985) vol. 82, 5131-5135.
Houghten, et al., *Peptide Chemistry*, (1987) 295-298.
Beaucage, et al., *Tetrahedron Lett.*, (1981) vol. 22, 1859-1862.
Matteneci, et al., *J. Am. Chem. Soc.*, (1981) vol. 103, 3185-3191.
Green, et al., "Iontophoretic Delivery of a Series of Tripeptides Across the Skin in Vitro," *Pharmaceutical Research*, (1991) vol. 8 No. 9, 1121-1127.
Markussen, et al., "Soluble, Prolonged-Acting Insulin Derivatives. III. Degree of Protraction, Crystallizability, and Chemical Stability of Insulins Substituted in Positions A21, B13, B23, B27, and B30," *Protein Engineering*, (Jul. 1988) vol. 2 No. 2, 157-166.
Lohse, et al., "Three Genetic Variants of Human Plasma Apolipoprotein A-IV" *J. Biol. Chem.* (Jul. 25, 1991) vol. 266 No. 21, 13513-13518.
Green, et al., "Transdermal iontophoresis of amino acids and peptides in vitro," *J. of Controlled Release*, (1992) 21:187-190.
Reichardt, et al., "Molecular characterization of two galactosemia mutations: correlation of mutations with highly conserved domains in galactose-1-phosphate uridyl transferase," *Am. J. Hum. Genet.*, (1991) vol. 49(4):860-7.
Nishimura, et al., "Factor IX Fukuoka. Substitution of ASN92 by His in the second epidermal growth factor-like domain results in defective interaction with factors VIIa/X," *J. Biol. Chem.*, (1993) 24041-6.
Levine, B. et a;., "Molecular Analysis of Neurovirulent Strains of Sindbis Virus that Evolve during Persistent Infection of *scid* Mice", *Journal of Virology*, 1993, (67)11, 6872-6875.

* cited by examiner

Primary Examiner—David J. Steadman

(57) ABSTRACT

Methods of modifying polypeptide drugs in order to enhance their transdermal electrotransport flux are provided. The polypeptide is modified by substituting a histidine residue (His) for one or more glutamine (Gln), threonine (Thr) and/or asparagine (Asn) residue(s). The His for Gln substitution is particularly preferred from the standpoint of retaining biological activity of the parent polypeptide. Compositions containing the modified polypeptide, which are useful for transdermal electrotransport delivery, are also provided.

16 Claims, 1 Drawing Sheet

METHOD OF ENCHANCING ELECTRONTRANSPORT POLYPEPTIDE FLUX BY AMINO ACID SUBSTITUTION WITH HISTIDINE

CROSS REFERENCE TO RELATED APPLICATIONS

This application is a continuation of U.S. patent application Ser. No. 08/466,610, filed Jun. 6, 1995.

TECHNICAL FIELD

The invention relates generally to electrotransport drug delivery, and more particularly to transdermal electrotransport drug delivery. Specifically, the invention relates to a method of improving electrotransport flux of polypeptide drugs by replacing certain amino acids in the polypeptide.

BACKGROUND OF THE INVENTION

Transdermal (i.e., through the skin) delivery of therapeutic agents (e.g., drugs) is an important medicament administration route. Transdermal drug delivery bypasses gastrointestinal degradation and hepatic metabolism. Most commercial transdermal drug delivery systems (e.g., nitroglycerin, scopolamine, estradiol, testosterone skin patches) deliver drug by passive diffusion. The drug diffuses from a reservoir in the patch into the skin of the patient by means of the concentration gradient which exists, i.e., the drug diffuses from the high concentration in the patch reservoir to the low concentration in the patient's body. The flux of drug through a patient's skin is determined by a number of factors including the drug's partition coefficient and solubility characteristics. This type of delivery system (i.e., a patch) provides slow, but controlled, delivery of the drug to a patient's blood stream. Transdermal drug delivery is an especially attractive administration route for drugs with a narrow therapeutic index, short half-life and potent activity.

Unfortunately, many drugs exhibit transdermal diffusion fluxes which are too low to be therapeutically effective. This is especially true for high molecular weight drugs such as polypeptides and proteins. To enhance transdermal drug flux, a technique involving application of low levels of electric current applied through a drug reservoir in contact with a patient's body surface (e.g., skin) has been used. This technique has been called by several names including iontophoresis and, more recently, electrotransport.

Electrotransport is a process by which the transdermal transport of therapeutic agents or species is achieved by using an electrical current as the driving force, i.e., by the application of an electric current to the patient through an agent-containing reservoir. As such, electrotransport is a more controllable process than passive transdermal drug delivery since the amplitude, timing and polarity of the applied electric current is easily regulated using standard electrical components. In general, electrotransport drug flux can be from 50% to several orders of magnitude greater than passive transdermal flux of the same drug.

In presently known electrotransport devices, at least two electrodes are used. Both of these electrodes are positioned in intimate electrical contact with some portion of the patient's body surface (e.g., skin). One electrode, called the active or donor electrode, is the electrode from which the (e.g., ionic or ionizable) therapeutic agent, drug precursor or drug is delivered into the body by electrotransport. The other electrode, called the counter or return electrode, serves to close the electrical circuit through the body. In conjunction with the patient's body surface contacted by the electrodes, the circuit is completed by connection of the electrodes to a source of electrical energy, e.g., a battery.

Depending upon the electrical charge of the species to be delivered transdermally, either the anode or cathode may be the "active" or donor electrode. If, for example, the ionic substance to be delivered into the body is positively charged (i.e., a cation), then the anode will be the active electrode and the cathode will serve to complete the circuit. On the other hand, if the ionic substance to be delivered is relatively negatively charged (i.e., an anion), then the cathodic electrode will be the active electrode and the anodic electrode will be the counter electrode.

Alternatively, both the anode and the cathode may be used to deliver drugs of appropriate charge into the body. In such a case, both electrodes are considered to be active or donor electrodes. That is to say, the anodic electrode can deliver positively charged agents into the body while the cathodic electrode can deliver negatively charged agents into the body.

Existing electrotransport devices generally require a reservoir or source of the therapeutic agent that is to be delivered into the body by electrotransport; the agent is typically in the form of a liquid solution of an ionized or ionizable species, or a precursor of such species. Examples of such reservoirs or sources include a pouch as described in Jacobsen, U.S. Pat. No. 4,250,878; a pre-formed gel body as disclosed in Webster, U.S. Pat. No. 4,382,529; and a glass or plastic container holding a liquid solution of the drug as disclosed in the figures of Sanderson et al., U.S. Pat. No. 4,722,726. Such drug reservoirs are electrically connected to the anode or to the cathode of the electrotransport device to provide a fixed or renewable source of one or more desired species or agents.

The term "electrotransport" as used herein, refers generally to the electrically assisted delivery of a therapeutic agent, whether the agent to be delivered is completely charged (i.e., 100% ionized), completely uncharged, or partly charged and partly uncharged. The therapeutic agent or species may be delivered by electromigration, electroosmosis, electroporation or any combination thereof. Electroosmosis, in general, results from the migration of liquid solvent, in which the species is contained, as a result of the application of electromotive force to the therapeutic species reservoir. Electroporation involves the formation of transiently existing pores which occur upon applying electric current to the skin.

Of particular interest is the transdermal electrotransport delivery of peptides, polypeptides, and proteins because of the problems encountered with more common drug administration routes such as oral delivery. Polypeptide and protein molecules are highly susceptible to degradation by proteolytic enzymes in the gastrointestinal tract and are subjected to an extensive hepatic metabolism when taken orally. Polypeptides and proteins usually require parental administration to achieve therapeutic levels in the patient's blood. The most conventional parenteral administration techniques are hypodermic injections and intravenous administration. Polypeptides and proteins are, however, inherently short acting in their biological activity, requiring frequent injections, often several times a day, to maintain the therapeutically effective levels needed. Patients frequently find this treatment regimen to be inconvenient, painful and with an attendant risk of, e.g., infection.

Much effort has been expended to find other routes (other than parenteral injections) for effective administration of pharmaceutical polypeptides and proteins. Administration routes with fewer side effects as well as better patient compliance have been of particular interest. Such alternative routes have generally included "shielded" oral administration wherein the polypeptide/protein is released from a capsule or other container after passing through the low pH environment of the stomach, delivery through the mucosal tissues, e.g., the mucosal tissues of the lung with enhalers or the nasal mucosal tissues with nasal sprays, and implantable pumps. Unfortunately to date, these alternative routes of polypeptide/protein delivery have met with only limited success.

Electrotransport delivery of polypeptides and proteins has also encountered technical difficulties. For example, water is the preferred liquid solvent for forming the solution of the drug being delivered by electrotransport due to its excellent biocompatability. Unfortunately, many polypeptides and proteins are unstable (i.e., they become hydrolyzed, oxidized, denatured or otherwise degraded) in the presence of water. The skin also contains proteolytic enzymes which may degrade the polypeptide/protein as it is delivered transdermally. In addition, certain polypeptides/proteins, particularly those that are not native to the animal being treated, may cause skin reactions, e.g., sensitization or irritation.

A number of investigators have disclosed electrotransport delivery of polypeptides and proteins. An early study by R. Burnette et al., *J. Pharm. Sci.*, vol. 75 (1986) 738, involved the in vitro skin permeation of thyrotropin releasing hormone, a small tripeptide molecule. The electrotransport flux was found to be higher than passive diffusional flux. Chien et al., *J. Pharm. Sci.*, vol. 78 (1988) 376, in both in vitro and in vivo studies, showed that transdermal delivery of vasopressin and insulin via electrotransport was possible. See, also, Maulding et al., U.S. Statutory Invention Registration No. H1160, which discloses electrotransport delivery of calcitonin in minipigs.

A number of approaches (other than simply increasing the applied levels of electrotransport current) have been used to enhance transdermal electrotransport flux of polypeptide and protein drugs. One approach involves the use of flux enhancers such as ionic surfactants. See, e.g., Sanderson et al., U.S. Pat. No. 4,722,726. Another approach uses cosolvents other than just water to enhance electrotransport flux. See, e.g., European Patent Application 0278 473. Yet another approach involves mechanically disrupting the outer layer (i.e., the straum corneum) of the skin prior to electrotransport delivery therethrough. See, e.g., Lee et al., U.S. Pat. No. 5,250,023.

Further approaches to enhancing transdermal electrotransport drug flux involve creating a prodrug or an analog of the drug of interest and electrotransporting the prodrug or modified analog. For example, WO 92/12999 discloses delivery of insulin as an insulin analog having a reduced tendency to self-associate (apparently associated forms of insulin present in conventional pharmaceutical compositions reduce transdermal delivery of the insulin). The analogs are created by substituting aspartic acid (Asp) or glutamic acid (Glu) for other amino acid residues at selected positions along the insulin polypeptide chain. WO 93/25197 discloses delivery of both peptide and non-peptide drugs as pharmaceutical agent-modifier complexes or prodrugs wherein a chemical modifier (e.g., a charged moiety) is covalently bonded to the parent pharmaceutical agent. The covalent bond is broken after the agent is delivered into the body, thereby releasing the parent agent.

While the problems associated with electrotransport delivery of proteins and polypeptides have been recognized and attempts to improve the electrotransport flux of polypeptide and protein drugs have been advanced, there still exists a need to provide a method for achieving higher transdermal electrotransport flux of polypeptides and proteins.

DESCRIPTION OF THE INVENTION

It is an aspect of the present invention to provide a method for increasing electrotransport flux of drugs, and more specifically, polypeptide and protein drugs.

It is another aspect of the present invention to provide a method for increasing transdermal electrotransport flux of polypeptide and protein drugs. As such, the method of the present invention permits electrotransport delivery of many polypeptides and proteins which heretofore could not be delivered transdermally by electrotransport at therapeutically effective rates.

These and other aspects will become apparent to persons skilled in the electrotransport delivery field from the following detailed description of the present invention. The present invention relates to methods of derivatizing polypeptide and protein drugs so as to improve or enhance the electrotransport flux of the drug. The method of the present invention is characterized by providing the polypeptide or protein of interest as a synthetic analog which has improved electrotransport flux properties such as increased positive charge at the pH at which electrotransport occurs, increased electrophoretic mobility and/or increased hydrophilicity.

The analog preferably has at least about the same bioactivity of the parent polypeptide or protein, and more preferably has greater bioactivity than the parent. The analog differs from the parent by way of substitution of histidine residues for one or more amino acid residues that have a polar but uncharged side chain. The histidine residues exhibit a positive charge at pH ranges which are typically encountered during anodic electrotransport delivery. The preferred substitutable amino acid residues include glutamine, asparagine and threonine. Of these, glutamine is most preferably substituted.

In another aspect, the invention is a synthetic analog having enhanced electrotransport flux compared to its parent polypeptide or protein drug. The parent protein or polypeptide drug has at least one polar but uncharged side chain amino acid residue, and the analog has at least one of these residues substituted by a histidine residue. The analog preferably exhibits at least about the same biological activity of the parent protein or polypeptide drug and preferably has the same overall charge distribution of the parent at physiological pH.

Other advantages and a fuller appreciation of specific adaptations, compositional variations, and physical attributes of the present invention will become apparent from the following drawing and detailed description.

BRIEF DESCRIPTION OF THE DRAWING

In the drawing, wherein like reference numerals refer to like elements throughout.

MODES FOR CARRYING OUT THE INVENTION

Figure 1:
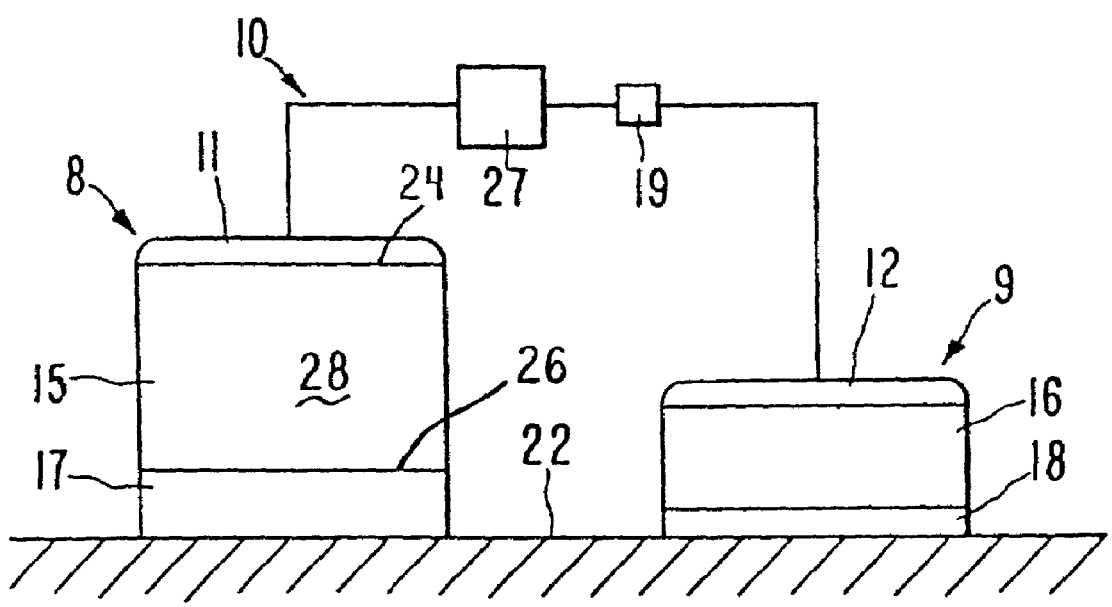
FIG. 1 is a schematic view of an electrotransport drug delivery device in accordance with the present invention.

The present invention relates broadly to a method for increasing the electrotransport flux of therapeutic agents, and particularly the transdermal electrotransport flux of polypeptides and proteins. The present invention also relates to therapeutic agent formulations and electrotransport delivery systems for practicing the methods described herein.

The present invention is characterized by an ability to improve the electrotransport flux of polypeptide and protein drugs for electrotransport delivery by increasing both the hydrophilicity and electrophoretic mobility at the pH of electrotransport while retaining overall charge distribution at approximately physiological pH, and preferably also retaining at least about the same biological activity of the polypeptide or protein drug.

In one aspect, the present invention provides a synthetic analog of a biologically active polypeptide drug having enhanced electrotransport characteristics compared to the drug. As used herein, the term "polypeptide," is meant to be construed broadly to include any amino acid residues linked by peptide bonds; namely, peptides, polypeptides and proteins. As used herein, the term "analog" is meant to be construed broadly as referring to a mutein, a structural derivative of a parent polypeptide drug, or a modified polypeptide in which at least one amino acid residue in the parent polypeptide drug has been replaced with a different amino acid residue. The parent drug may be derived from natural sources or wholly synthesized by chemical or biochemical means. It is understood that the parent drug may be a naturally occurring polypeptide sequence or may itself have structural differences from a naturally occurring polypeptide. The terms "polypeptide drug," "polypeptide agent" or "pharmaceutical polypeptide" are all meant to refer to any polypeptide, as that term is used herein, that has physiologic activity, i.e., bioactivity.

According to this aspect of the invention, preferred as polypeptide drugs are those which contain at least one amino acid residue having a polar but uncharged side chain. The analog in accordance with the present invention is synthesized by replacing at least one of these residues with a histidine (His) residue. Specifically preferred as polypeptide drugs are those which contain at least one glutamine (Gln), threonine (Thr) or asparagine (Asn) residue. One or more of these residues are replaced with a histidine (His) residue in the analog of the present invention. Most preferred is the replacement of glutamine residue(s) on the polypeptide drug with histidine residues.

The analog in accordance with the present invention preferably exhibits biological activity at least about the same as that of the unmodified polypeptide drug of interest, and more preferably has greater bioactivity than the drug, but has increased hydrophilicity and electrophoretic mobility compared to the parent drug. As such, the analog in accordance with the present invention exhibits enhanced transdermal electrotransport flux relative to the parent drug, i.e., the unmodified polypeptide.

The present invention is useful to increase the net positive charge on a polypeptide which is delivered from an anodic reservoir of an electrotransport delivery device. Generally speaking, the pH range of an anodic donor reservoir formulation containing the analog polypeptide is in the pH range of about 3.5 to about 8, and preferably about 5 to 6. At these pH ranges, the replacement of His for Gln, Asn or Thr results in increased hydrophilicity of the analog compared to the parent drug or unmodified polypeptide due to the positive charge on the imidazole ring and increased electrophoretic mobility due to the higher net positive charge. The result is that the analog exhibits increased transdermal electrotransport flux compared to the parent drug. At the same time at physiological pH, namely, pH=7.4, the analog retains the charge, hydrogen bonding and hydrophobicity characteristics of the parent polypeptide drug. At neutral pH, the imidazole side chain of His is not charged, and thus, the replacement of His for Gln, Asn or Thr does not decrease the biological activity of the analog appreciably, i.e., the substitution does not alter the affinity of the analog for its intended receptor.

It is further contemplated that the number of His substitutions for Gln, Asn or Thr is limited only by the desired net charge at the pH used in the electrotransport system. However, the number of substitutions should not be so numerous that the analog is recognized as a foreign protein by the patient's immune system. While there are no absolute rules for determining the number of substitutions before a polypeptide or protein is viewed as "foreign," the closer the analog is in structure/amino acid sequence to the parent (i.e., the fewer the substitutions), the less likely the polypeptide/protein will be viewed by the body's immune system as being foreign.

Typically, polypeptides and proteins, including the analogs thereof, within the scope of the present invention have molecular weights in the range of about a few hundred daltons (e.g., for a tripeptide) to about 30,000 daltons. Specific examples of polypeptide, protein and macromolecule drugs in this range include, without limitation, CSF's, GHRH, insulin, calcitonin, endorphins, erythropoietin, parathyroid hormone and agonists, GHRF, insulinotropin, octreotide, pituitary hormones (e.g, HGH, HMG, desmopressin acetate, etc.), follicle luteoids, αANF, growth factors such as growth factor releasing factor (GFRF), somatostatin, atrial natriuretic peptide, bradykinin, somatotropin, platelet-derived growth factor, asparaginase, chymopapain, cholecystokinin, chorionic gonadotropin, corticotropin (ACTH), epidermal growth factor, erythropoietin, glucagon, hirulog, hyaluronidase, interferons, insulin-like growth factors (e.g., IGF-1), interleukins, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, CD4, ceredase, FAB fragments, IgE peptide suppressors, neuropeptide Y, neurotrophic factors, opiate peptides, parathyroid hormone antagonists, protein C, protein S, renin inhibitors, α-1-thymosin, thrombolytics, TNF, vaccines, vasopressin antagonist analogs, α-1-anti-trypsin (recombinant), and β-TGF.

Illustrative examples of polypeptide drugs which are well-suited for modification in accordance with the present invention are granulocyte-colony stimulating factor (G-CSF), a factor that stimulates the production of granulocytes, particularly neutrophils; parathyroid hormone (PTH), a regulator factor in the homeostatic control of calcium and phosphate metabolism, and used to treat osteoporosis; luteinizing hormone releasing hormone (LHRH) and its analogs, and growth hormone releasing hormone (GHRH) and its analogs, with enhanced transdermal flux therefor.

Replacing His for Gln, Asn or Thr in accordance with the present invention is viewed as a "conservative" modification or derivatization of a polypeptide or protein. By this it is meant that the hydrophobicity, net charge at physiological pH, volume, and hydrogen bonding capacities of the parent polypeptide or protein are preserved in the analog. The preferred substitution of His for Gln is the most conservative of the three possible substitutions since the hydrogen bonding capacities, charges at pH 7, and side chain volumes of the. analog so synthesized are virtually identical to the parent compound.

The side chain structures of Gln and His residues are shown below:

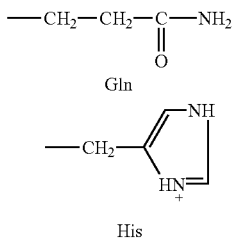

The side chains of the Gln and His residues reveal a considerable similarity in the geometries of hydrogen bonding capability, i.e., the replacement of Gln by His does not appreciably alter the hydrogen bonding capacity of the side chain. Depending on the bond angles between the planar amide group, the β CH$_2$ and the α CH$_2$, hydrogen bonds involving the Gln side chain can also be made by a His side chain.

Further, the hydrophobicities of His (uncharged state) and Gln residues are very similar. See, Tanford et al., *J. Biol. Chem.*, vol. 246 (1971) 2211-2217, where the hydrophobicities of amino acid side chains in both water and various alcohols were measured, and very similar transfer free energies for His and Gln were found in moderate concentrations of dioxane.

The analogs in accordance with the present invention can be synthesized in a number of ways known and conventional in the art, and therefore, are not described in detail herein. Such methods include de novo solid phase synthesis of the polypeptides, wet chemistry methods and biotechnological methods.

Solid phase protein synthesis utilizes the attachment of the first amino acid of the desired sequence by its carboxyl group to an insoluble resin. Once the desired product is obtained the peptide sequence is cleaved from the resin. See, e.g., R. B. Merrifield et al., *Biochemistry*, vol. 21 (1981) 5020; M. Bodanszky, "Principles of Peptide Synthesis," Akad.-Verlag (1984); J. M. Stewart et al. "Solid Phase Peptide Synthesis," Freeman (1969), the disclosures of which are incorporated herein by reference. Other synthetic methods are also known. For example, the analogs described herein can be prepared by the method of simultaneous multiple peptide synthesis. See, e.g., Houghten, *Proc. Natl. Acad. Sci. U.S.A.*, vol. 82 (1985) 5131-5135; Houghten et al., *Peptide Chemistry*, (1987) 295-298; U.S. Pat. No. 4,631,211, the disclosures of which are incorporated herein by reference.

The analogs can also be synthesized by programming a commercial peptide synthesizer apparatus such that some to all of the glutamine residues in the amino acid sequence of a polypeptide or protein drug of interest are replaced by histidine residues.

The analogs of the present invention can also be synthesized by known genetic engineering techniques, such as recombinant expression systems. In vitro mutagenesis can be utilized to alter the parent polypeptide gene through replacement of the appropriate bases in the gene at the appropriate site with others to encode for the desired amino acid residue substitute. For example, the replacement of some to all of the codons for Gln by the codon for His requires only a single-base replacement of the A or G in the last position of the Gln codon with a U or C. The gene encoding the desired analog is then inserted into a suitable expression vector which when transferred to a suitable host organism, e.g., *E. Coli*, Bacillus or yeast, generates the desired analog. The expressed analog is then isolated from the cells or the culture broth depending on whether the expressed analog is secreted from the cells or not. In the expressed analog, some to all of the glutamine residues do not occur in the polypeptide sequence, but substituted in those locations in the sequence are histidine residues. Methods of identifying and isolating genes encoding analog peptides and proteins of interest, or for constructing such genes, and expressing them in host systems are well understood and developed. These processes are described in patents and in other literature. See, e.g., U.S. Pat. Nos. 4,431,739 and 5,013,653; and Sambrook et al., "Molecular Cloning: A Laboratory Manual," 2d ed., Cold Spring Harbor (1989); "ACS Symposium Series, 477: Expression Systems and Processes of rDNA Products," R. T. Hatch et al., American Chemical Society (1991); R. Seetharam et al., "Purification and Analysis of Recombinant Proteins" in "Bioprocess Technology," vol. 12, Marcel Dekker (1991), the disclosures of which are incorporated herein by reference.

The altered gene structure can also be constructed by automated synthetic techniques, by, for example, the phosphoramide method of solid-phase synthesis of oligonucleotides. See, e.g., S. L. Beaucage et al., *Tetrahedron Lett.*, vol. 22 (1981) 1859-1862; M. D. Matteneci et al., *J. Am. Chem. Soc.*, vol. 103 (1981) 3185-3191, the disclosures of which are incorporated herein by reference.

While illustrative examples of the analogs contemplated by the present invention are given hereinafter for G-CSF, parathyroid hormone and human growth hormone releasing hormone, the following teachings apply to any other biologically active proteins or polypeptides that contain substitutable residues.

Human granulocyte-colony stimulating factor (hG-CSF), a 174 amino acid residue polypeptide, is known to have 12 Gln residues which are at positions 11, 20, 25 and 32 in the A helix; 107, 119 and 120 in the C helix; 145, 158 and 173 in the D helix; and 131 and 134 in the loop region (SEQ ID NO:1). Substitution of one or more up to and including all of the Gln's of G-CSF with His residues produces an analog which exhibits a specific activity close to that of unmodified or parent G-CSF. Examples of G-CSF analogs in accordance with the present invention include: His(11) G-CSF (SEQ ID NO:2); His(11), His(20) G-CSF (SEQ ID No:3).

Human parathyroid hormone (h-PTH), a protein having a molecular weight of about 9,500 daltons, has a polypeptide sequence of about 34 amino acid residues from the N-terminal which exhibits full biological activity. The 34 amino acid sequence is reported to have two glutamine residues at positions 6 and 29 of the polypeptide chain. (SEQ ID NO:5.) As in the case of G-CSF, it is possible to use the present invention to create mutations at codons 6 and 29 of the parathyroid hormone gene that results in one or both of the Gln residues being replaced with His residues. Such analogs in accordance with the present invention include: His (5) PTH (SEQ ID NO:6); His(5), His(29) PTH (SEQ ID NO:7).

Human growth hormone releasing hormone (h-GHRH) is a 44 amino acid polypeptide containing glutamine residues at positions 16, 24, 30, 31 and 36 (SEQ ID NO:8). As in the case of hG-CSF, a modified h-GHRH gene can be prepared by inducing site-specific mutagenesis in the h-GHRH gene at codons specifying positions 16, 24, 30, 31, 36 or any combination of two or more positions which preserve or increase biological activity. Preferably, oligonucleotide-directed mutagenesis may be employed to make an analog h-GHRH gene that encodes an analog having h-GHRH activity but having Gln 31 and 36 changed to His 31 and 36; namely, His(31), His(36) h-GHRH (SEQ ID NO:9).

The analogs of the present invention are particularly well suited for electrotransport delivery through a body surface or membrane (e.g., skin) of an animal (e.g., a human or other mammals such as cattle, horses, pigs, etc.). Thus, the present invention provides a method of administering an analog to a patient by electrotransport, comprising the steps of providing a polypeptide, in the form of a synthetic analog, in a donor reservoir adapted to be placed in analog-transmitting relation with a body surface of the patient, and applying an electric field to the reservoir to transport the analog through the body surface by electrotransport. The (e.g., transdermal) electrotransport flux of the analog is higher than the (e.g., transdermal) electrotransport flux of the parent drug under similar conditions (i.e., applied electrotransport current, pH, drug concentration, etc.).

The method of the present invention may be performed using an electrically powered transdermal electrotransport delivery device having a donor reservoir, a reservoir containing the analog and configured and dimensioned to be placed in analog-transmitting relation with the skin, and a source of electrical power. The power source applies an electrical current to the reservoir which causes electrotransport delivery of the analog from the agent reservoir and through the body surface. The analog has one or more, up to and including all, of its Gln residues substituted with His residues (i.e., compared to the parent polypeptide or protein structure) and preferably exhibits a biological activity at least about the same as that of the parent polypeptide.

In a further aspect, the invention provides a therapeutic composition which comprises a donor reservoir formulation with a sufficient amount of a synthetic analog of a polypeptide parent drug to be therapeutically effective when delivered by electrotransport. The analog has at least one of one or more Gln residues of the parent polypeptide drug substituted with His residues. The analog preferably exhibits a biological activity at least about the same as, or preferably greater than, that of the parent protein or polypeptide.

The method and formulation of the present invention is not limited to an electrotransport device of any one particular structure. One example of an electrotransport delivery device 10 for use in the present invention, for delivery of an analog through a body surface 22 (typically intact skin or a mucosal membrane) is illustrated in FIG. 1.

Electrotransport delivery device 10 includes a donor electrode assembly 8 and a counter electrode assembly 9. Electrode assemblies 8 and 9 are electrically connected to an electrical power source 27, which is typically one or more low voltage batteries, and an optional control circuit 19. When the device 10 is placed on the skin or mucosal membrane of, e.g., a patient, the circuit between the electrodes is closed, and the power source begins to deliver current through the device and through the skin or mucosal membrane of the patient. The donor and counter electrode assemblies 8 and 9 normally include a strippable release liner (not shown in FIG. 1) which is removed prior to application of electrode assemblies 8 and 9 to body surface 22.

The donor electrode assembly 8 includes a donor electrode 11 and an agent reservoir 15. The agent reservoir 15 contains the analog to be delivered by electrotransport from device 10. The donor electrode assembly 8 is suitably adhered to the body surface 22 by means of an ion-conducting adhesive layer 17.

Device 10 includes a counter electrode assembly 9 which is placed on the body surface 22 at a location spaced apart from electrode assembly 8. Counter electrode assembly 9 includes a counter electrode 12 and an electrolyte reservoir 16. Counter electrode assembly 9 is suitably adhered to the body surface 22 by means of an ion-conducting adhesive layer 18.

Electrodes 11 and 12 are electrically conductive and may be formed of a metal, e.g., a metal foil or metal deposited or painted on a suitable backing. Examples of suitable metals include silver, zinc, silver/silver chloride, aluminum, platinum, stainless steel, gold and titanium. Alternatively, the electrodes 11 and 12 may be formed of a polymer matrix containing a conductive filler such as a metal powder, powdered graphite, carbon fibers or other known electrically conductive filler material(s).

Electrodes 11 and 12 are electrically connected to power source 27 using well known means, e.g., printed flexible circuits, metal foils, wires or by direct contact.

The electrolyte reservoir 16 contains a suitable pharmacologically acceptable salt. Suitable salts include sodium chloride, alkali metal salts, alkaline earth metal salts such as chlorides, sulfates, nitrates, carbonates, phosphates, and organic salts such as ascorbates, citrates, acetates and mixtures thereof. Reservoir 16 optionally may contain a buffering agent.

Reservoirs 15 and 16 are preferably comprised of any material adapted to absorb and hold a sufficient quantity of liquid (i.e., a liquid solution of the analog) therein in order to permit the passage of the analog therethrough by electrotransport. Preferably, the reservoirs contain one or more hydrophilic polymers such as polyvinylpyrrolidone, polyvinyl alcohol, or polyethylene glycols, and optionally one or more hydrophobic polymers such as polyisobutylene, polyethylene, or polypropylene. While not limited to any particular shape or volume, reservoirs 15 and 16 each typically have a thickness of 0.6 cm (¼ inch) or less and a cross sectional (e.g., skin contact) area in the range of about 1 to 50 cm². The analog may be added to the polymeric reservoir 15 matrix by conventional means such as mixing in a liquid state and later molding or extruding the analog-containing reservoir matrix.

The electrotransport current applied by the device is typically in the range of about 50 to 400 µA/cm².

The transdermal electrotransport flux of analogs in accordance with the present invention is expected to be at least about 20% higher, and more preferably at least about 50%-100% higher than that of the parent polypeptide.

The present invention is further explained by the following examples which should not be construed by way of limiting the scope of the present invention.

EXAMPLE 1 hG-CSF Analog

Human G-CSF (hG-CSF) is a pharmaceutical protein used to treat patients recovering from chemotherapy. It is also used as an adjunct therapy for treating bacterial infections. An analog of G-CSF is prepared according to the known and conventional methods described hereinbefore in which glutamine residues at positions 107, 119, 120, 131, 134, 145, 158 and 173 are replaced with histidine residues (SEQ ID NO:4). This analog has a net charge at pH 6 of close to +4.

An anodic donor reservoir is prepared comprising an aqueous solution of the G-CSF analog in a hydroxyethyl cellulose (HEC) hydrogel matrix. The formulation contains 5 mg/mL hG-CSF analog in 5 mM pH 6 histidine buffer in a 3% HEC hydrogel containing 1% glycerol.

The hG-CSF analog-containing donor reservoir is used in an electrotransport delivery device. The delivery device includes a silver foil anodic electrode placed on one surface of the donor reservoir, and a silver chloride counter-electrode placed on a surface of an HEC hydrogel matrix containing a buffered saline solution and used as the counter electrode/reservoir assembly. The electrodes are connected by electrically-conductive adhesive strips to the outputs of an electrotransport current generating and controlling circuit which supplies a current of 2.0 mA. Each of the donor and counter HEC reservoirs has a skin contact area of 20 cm$^2$. The device is placed on a patient's skin, and applies an electrotransport current density of 100 μA/cm$^2$. The device is adapted to be worn over a period of time up to 24 hours, during which the device continuously applies 2.0 mA of electrotransport current and, hence, delivers the G-CSF analog continuously over the 24-hour period.

After initiating electrotransport, blood samples are collected periodically, heparinized, centrifuged and the plasma stored at −80° C. Plasma concentrations of the analog are determined by an enzyme linked immunoassay method. The results show increased plasma levels compared to a control of electrotransport of the unmodified hG-CSF.

EXAMPLE 2 h-PTH Analog

Human parathyroid hormone (h-PTH) is a pharmaceutical polypeptide used to treat osteoporosis. An example of an analog of h-PTH is one in which the glutamine residue at position 29 is replaced by histidine to increase the net charge by about +1 at pH 5. Replacement of the glutamine residue at position 29 retains the approximate biological activity of the parent compound (SEQ ID NO:7).

An anodic donor reservoir is prepared comprising an aqueous solution of the h-PTH analog in an HEC hydrogel matrix. The formulation contains 10 mg/mL PTH analog in 5 mM pH 5 acetate buffer in a 3% HEC hydrogel containing 1% glycerol.

The h-PTH analog-containing donor reservoir is used in a device similar to that described in Example 1 hereinbefore except that the electrotransport current generating and control circuit operates in one of two modes. The first mode is a continuous delivery mode as described in Example 1, and the second is an intermittent delivery mode wherein the release of h-PTH analog occurs periodically over predetermined intervals throughout the day.

Blood samples are collected and analyzed as described in Example 1, and the results show improved electrotransport plasma levels compared to the unmodified h-PTH.

EXAMPLE 3 h-GHRH Analog

Human GHRH (h-GHRH) is used to treat growth deficient (i.e., short) children and frail elderly adult patients. An analog of h-GHRH is prepared in which the glutaminyl residues at positions 16, 24, 30 and 31 are replaced by histidyl residues (SEQ ID NO:10). Such an analog would have the net charge increased by about +4 at pH 5.

An anodic donor reservoir is prepared comprising an aqueous solution of the h-GHRH analog in an HEC hydrogel matrix. The formulation contains 4 mg/mL h-GHRH analog in 5 mM pH 5 acetate buffer in 3% HEC hydrogel containing 1% glycerol.

The h-GHRH analog-containing donor reservoir is used in a device as described in Example 1. The device is placed on a patient's skin and delivers h-GHRH analog continuously over the 24-hour wearing period.

Blood samples are collected and analyzed as described in Example 1, and the results show improved electrotransport and plasma levels compared to unmodified h-GHRH.

In summary, the substitution of histidine residues for glutamine, asparagine or threonine residues in polypeptide drugs provides improved electrotransport properties, because the two amino acids have very similar hydrophobicity and similar tendency to not form an alpha helix. They have the same charge at physiological pH, and have almost exactly the same hydrogen bonding geometry and capability.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

The invention claimed is:

1. A method for delivering a pharmaceutical polypeptide agent through a body surface comprising:
   (a) preparing a synthetic analog of the parent human growth hormone releasing hormone (SEQ ID NO:8) by replacing at least one glutamine residue at position 16, 30, 31, or 36 of the parent human growth hormone releasing hormone with a histidine residue; and
   (b) delivering the synthetic analog through the body surface by electrotransport.

2. The method of claim 1 wherein the synthetic analog is prepared by replacing the glutamine residues at positions 31 and 36 of the parent human growth hormone releasing hormone with histidine residues.

3. The method of claim 1 wherein the synthetic analog has increased hydrophilicity and electrophoretic mobility relative to that of the parent human growth hormone releasing hormone.

4. The method of claim 1 wherein the synthetic analog exhibits at least about the same type and amount of biological activity as the parent human growth hormone releasing hormone.

5. The method of claim 1 wherein the overall charge of the synthetic analog is positive at a pH in the range of about 5 to 6 but substantially isoelectric at pH 7.4.

6. The method of claim 5 wherein the synthetic analog has a greater positive charge at a pH in the range of about 5 to 6 than the parent human growth hormone releasing hormone.

7. The method of claim 1 wherein the synthetic analog is provided in the form of an anodic donor reservoir formulation for delivering the synthetic analog through the body surface by electrotransport, the formulation having a pH in the range of about 3.5 to about 8.

8. The method of claim 7 wherein the formulation used for delivering the synthetic analog by electrotransport has a pH in the range of about 5 to about 6.

9. A method for delivering a pharmaceutical polypeptide agent through a body surface comprising:
   (a) preparing a synthetic analog of the parent human growth hormone releasing hormone (SEQ ID NO:8) by replacing at least two glutamine residues at positions 16, 24, 30, 31, or 36 of the parent human growth hormone releasing hormone with histidine residues; and
   (b) delivering the synthetic analog through the body surface by electrotransport.

10. The method of claim 9 wherein the synthetic analog is prepared by replacing the glutamine residues at positions 16, 24, 30, and 31 of the parent human growth hormone releasing hormone with histidine residues.

11. The method of claim 9 wherein the synthetic analog has increased hydrophilicity and electrophoretic mobility relative to that of the parent human growth hormone releasing hormone.

12. The method of claim 9 wherein the synthetic analog exhibits at least about the same type and amount of biological activity as the parent human growth hormone releasing hormone.

13. The method of claim 9 wherein the overall charge of the synthetic analog is positive at a pH in the range of about 5 to 6 but substantially isoelectric at pH 7.4.

14. The method of claim 13 wherein the synthetic analog has a greater positive charge at a pH in the range of about 5 to 6 than the parent human growth hormone releasing hormone.

15. The method of claim 9 wherein the synthetic analog is provided in the form of an anodic donor reservoir formulation for delivering the synthetic analog through the body surface by electrotransport, the formulation having a pH in the range of about 3.5 to about 8.

16. The method of claim 15 wherein the formulation used for delivering the synthetic analog by electrotransport has a pH in the range of about 5 to about 6.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 174 amino acids
      (B) TYPE: amino acid
      (D) TOPOLOGY: linear (ix) FEATURE:
      (A) NAME/KEY: Peptide
      (B) LOCATION: 1..174
      (D) OTHER INFORMATION: /note= "granulocyte-colony -continued stimulating factor"

(xi) SEQUENCE DESCRIPTION: SEQ ID NO: 1:

Thr Pro Leu Gly Pro Ala Ser Ser Leu Pro Gln Ser Phe Leu Leu Ly
1               5                   10                  15

Cys Leu Glu Gln Val Arg Lys Ile Gln Gly Asp Gly Ala Ala Leu Gl
            20                  25                  30

Glu Lys Leu Cys Ala Thr Tyr Lys Leu Cys His Pro Glu Glu Leu Va
            35                  40                  45

Leu Leu Gly His Ser Leu Gly Ile Pro Trp Ala Pro Leu Ser Ser Cy
        50                  55                  60

Pro Ser Gln Ala Leu Gln Leu Ala Gly Cys Leu Ser Gln Leu His Se
65                  70                  75                  80

Gly Leu Phe Leu Tyr Gln Gly Leu Leu Gln Ala Leu Glu Gly Ile Se
                85                  90                  95

Pro Glu Leu Gly Pro Thr Leu Asp Thr Leu Gln Leu Asp Val Ala As
            100                 105                 110

Phe Ala Thr Thr Ile Trp Gln Gln Met Glu Glu Leu Gly Met Ala Pr
            115                 120                 125

Ala Leu Gln Pro Thr Gln Gly Ala Met Pro Ala Phe Ala Ser Ala Ph
        130                 135                 140

Gln Arg Arg Ala Gly Gly Val Leu Val Ala Ser His Leu Gln Ser Ph
145                 150                 155                 160

Leu Glu Val Ser Tyr Arg Val Leu Arg His Leu Ala Gln Pro
                165                 170

(2) INFORMATION FOR SEQ ID NO: 2:

(i) SEQUENCE CHARACTERISTICS:
        (A) LENGTH: 174 amino acids
        (B) TYPE: amino acid
        (D) TOPOLOGY: linear (ix) FEATURE:
        (A) NAME/KEY: Peptide
        (B) LOCATION: 1..174
        (D) OTHER INFORMATION: /note= "modified granulocyte-colony
            stimulating factor"

(xi) SEQUENCE DESCRIPTION: SEQ ID NO: 2:

Thr Pro Leu Gly Pro Ala Ser Ser Leu Pro His Ser Phe Leu Leu Ly
1               5                   10                  15

Cys Leu Glu Gln Val Arg Lys Ile Gln Gly Asp Gly Ala Ala Leu Gl
            20                  25                  30

Glu Lys Leu Cys Ala Thr Tyr Lys Leu Cys His Pro Glu Glu Leu Va
            35                  40                  45

Leu Leu Gly His Ser Leu Gly Ile Pro Trp Ala Pro Leu Ser Ser Cy
        50                  55                  60

Pro Ser Gln Ala Leu Gln Leu Ala Gly Cys Leu Ser Gln Leu His Se
65                  70                  75                  80

Gly Leu Phe Leu Tyr Gln Gly Leu Leu Gln Ala Leu Glu Gly Ile Se
                85                  90                  95

Pro Glu Leu Gly Pro Thr Leu Asp Thr Leu Gln Leu Asp Val Ala As
            100                 105                 110

Phe Ala Thr Thr Ile Trp Gln Gln Met Glu Glu Leu Gly Met Ala Pr
            115                 120                 125

Ala Leu Gln Pro Thr Gln Gly Ala Met Pro Ala Phe Ala Ser Ala Ph
        130                 135                 140

```
Gln Arg Arg Ala Gly Gly Val Leu Val Ala Ser His Leu Gln Ser Ph
145                 150                 155                 160

Leu Glu Val Ser Tyr Arg Val Leu Arg His Leu Ala Gln Pro
                165                 170
```

(2) INFORMATION FOR SEQ ID NO: 3:

(i) SEQUENCE CHARACTERISTICS:
        (A) LENGTH: 174 amino acids
        (B) TYPE: amino acid
        (D) TOPOLOGY: linear (ix) FEATURE:
        (A) NAME/KEY: Peptide
        (B) LOCATION: 1..174
        (D) OTHER INFORMATION: /note= "modified granulocyte-colony
            stimulating factor"

(xi) SEQUENCE DESCRIPTION: SEQ ID NO: 3:

```
Thr Pro Leu Gly Pro Ala Ser Ser Leu Pro His Ser Phe Leu Leu Ly
1               5                   10                  15

Cys Leu Glu His Val Arg Lys Ile Gln Gly Asp Gly Ala Ala Leu Gl
                20                  25                  30

Glu Lys Leu Cys Ala Thr Tyr Lys Leu Cys His Pro Glu Glu Leu Va
                35                  40                  45

Leu Leu Gly His Ser Leu Gly Ile Pro Trp Ala Pro Leu Ser Ser Cy
                50                  55                  60

Pro Ser Gln Ala Leu Gln Leu Ala Gly Cys Leu Ser Gln Leu His Se
65                  70                  75                  80

Gly Leu Phe Leu Tyr Gln Gly Leu Leu Gln Ala Leu Glu Gly Ile Se
                85                  90                  95

Pro Glu Leu Gly Pro Thr Leu Asp Thr Leu Gln Leu Asp Val Ala As
                100                 105                 110

Phe Ala Thr Thr Ile Trp Gln Gln Met Glu Glu Leu Gly Met Ala Pr
                115                 120                 125

Ala Leu Gln Pro Thr Gln Gly Ala Met Pro Ala Phe Ala Ser Ala Ph
130                 135                 140

Gln Arg Arg Ala Gly Gly Val Leu Val Ala Ser His Leu Gln Ser Ph
145                 150                 155                 160

Leu Glu Val Ser Tyr Arg Val Leu Arg His Leu Ala Gln Pro
                165                 170
```

(2) INFORMATION FOR SEQ ID NO: 4:

(i) SEQUENCE CHARACTERISTICS:
        (A) LENGTH: 174 amino acids
        (B) TYPE: amino acid
        (D) TOPOLOGY: linear (ix) FEATURE:
        (A) NAME/KEY: Peptide
        (B) LOCATION: 1..174
        (D) OTHER INFORMATION: /note= "granulocyte-colony
            stimulating factor"

(xi) SEQUENCE DESCRIPTION: SEQ ID NO: 4:

```
Thr Pro Leu Gly Pro Ala Ser Ser Leu Pro Gln Ser Phe Leu Leu Ly
1               5                   10                  15

Cys Leu Glu Gln Val Arg Lys Ile Gln Gly Asp Gly Ala Ala Leu Gl
                20                  25                  30

Glu Lys Leu Cys Ala Thr Tyr Lys Leu Cys His Pro Glu Glu Leu Va
```

-continued

```
                35                  40                  45
Leu Leu Gly His Ser Leu Gly Ile Pro Trp Ala Pro Leu Ser Ser Cy
        50                  55                  60

Pro Ser Gln Ala Leu Gln Leu Ala Gly Cys Leu Ser Gln Leu His Se
 65                  70                  75                  80

Gly Leu Phe Leu Tyr Gln Gly Leu Leu Gln Ala Leu Glu Gly Ile Se
                85                  90                  95

Pro Glu Leu Gly Pro Thr Leu Asp Thr Leu His Leu Asp Val Ala As
            100                 105                 110

Phe Ala Thr Thr Ile Trp His His Met Glu Glu Leu Gly Met Ala Pr
            115                 120                 125

Ala Leu His Pro Thr His Gly Ala Met Pro Ala Phe Ala Ser Ala Ph
        130                 135                 140

His Arg Arg Ala Gly Gly Val Leu Val Ala Ser His Leu His Ser Ph
145                 150                 155                 160

Leu Glu Val Ser Tyr Arg Val Leu Arg His Leu Ala His Pro
                165                 170

(2) INFORMATION FOR SEQ ID NO: 5:

(i) SEQUENCE CHARACTERISTICS:
        (A) LENGTH: 34 amino acids
        (B) TYPE: amino acid
        (D) TOPOLOGY: linear (ix) FEATURE:
        (A) NAME/KEY: Peptide
        (B) LOCATION: 1..34
        (D) OTHER INFORMATION: /note= "parathyroid hormone"

(xi) SEQUENCE DESCRIPTION: SEQ ID NO: 5:

Ser Val Ser Glu Ile Gln Leu Met His Asn Leu Gly Lys His Leu As
 1               5                  10                  15

Ser Met Glu Arg Val Glu Trp Leu Arg Lys Lys Leu Gln Asp Val Hi
            20                  25                  30

Asn Phe (2) INFORMATION FOR SEQ ID NO: 6:

(i) SEQUENCE CHARACTERISTICS:
        (A) LENGTH: 34 amino acids
        (B) TYPE: amino acid
        (D) TOPOLOGY: linear (ix) FEATURE:
        (A) NAME/KEY: Peptide
        (B) LOCATION: 1..34
        (D) OTHER INFORMATION: /note= "modified parathyroid
            hormone"

(xi) SEQUENCE DESCRIPTION: SEQ ID NO: 6:

Ser Val Ser Glu Ile His Leu Met His Asn Leu Gly Lys His Leu As
 1               5                  10                  15

Ser Met Glu Arg Val Glu Trp Leu Arg Lys Lys Leu Gln Asp Val Hi
            20                  25                  30

Asn Phe (2) INFORMATION FOR SEQ ID NO: 7:

(i) SEQUENCE CHARACTERISTICS:
        (A) LENGTH: 34 amino acids
        (B) TYPE: amino acid
```

```
        (D) TOPOLOGY: linear (ix) FEATURE:
        (A) NAME/KEY: Peptide
        (B) LOCATION: 1..34
        (D) OTHER INFORMATION: /note= "modified parathyroid
            hormone"

(xi) SEQUENCE DESCRIPTION: SEQ ID NO: 7:

Ser Val Ser Glu Ile Gln Leu Met His Asn Leu Gly Lys His Leu As
1               5                   10                  15

Ser Met Glu Arg Val Glu Trp Leu Arg Lys Lys Leu His Asp Val Hi
            20                  25                  30

Asn Phe (2) INFORMATION FOR SEQ ID NO: 8:

(i) SEQUENCE CHARACTERISTICS:
        (A) LENGTH: 44 amino acids
        (B) TYPE: amino acid
        (D) TOPOLOGY: linear (ix) FEATURE:
        (A) NAME/KEY: Peptide
        (B) LOCATION: 1..44
        (D) OTHER INFORMATION: /note= "human growth hormone
            releasing hormone"

(ix) FEATURE:
        (A) NAME/KEY: Binding-site
        (B) LOCATION: 44
        (D) OTHER INFORMATION: /note= "carboxy terminal amide"

(xi) SEQUENCE DESCRIPTION: SEQ ID NO: 8:

Tyr Ala Asp Ala Ile Phe Thr Asn Ser Tyr Arg Lys Val Leu Gly Gl
1               5                   10                  15

Leu Ser Ala Arg Lys Leu Leu Gln Asp Ile Met Ser Arg Gln Gln Gl
            20                  25                  30

Glu Ser Asn Gln Glu Arg Gly Ala Arg Ala Arg Leu
        35                  40

(2) INFORMATION FOR SEQ ID NO: 9:

(i) SEQUENCE CHARACTERISTICS:
        (A) LENGTH: 44 amino acids
        (B) TYPE: amino acid
        (D) TOPOLOGY: linear (ix) FEATURE:
        (A) NAME/KEY: Peptide
        (B) LOCATION: 1..44
        (D) OTHER INFORMATION: /note= "modified hormone growth
            hormone releasing hormone"

(ix) FEATURE:
        (A) NAME/KEY: Binding-site
        (B) LOCATION: 44
        (D) OTHER INFORMATION: /note= "carboxy terminal amide"

(xi) SEQUENCE DESCRIPTION: SEQ ID NO: 9:

Tyr Ala Asp Ala Ile Phe Thr Asn Ser Tyr Arg Lys Val Leu Gly Gl
1               5                   10                  15

Leu Ser Ala Arg Lys Leu Leu Gln Asp Ile Met Ser Arg Gln His Gl
            20                  25                  30

Glu Ser Asn His Glu Arg Gly Ala Arg Ala Arg Leu
        35                  40
```

```
-continued (2) INFORMATION FOR SEQ ID NO: 10:

(i) SEQUENCE CHARACTERISTICS:
        (A) LENGTH: 44 amino acids
        (B) TYPE: amino acid
        (D) TOPOLOGY: linear (ix) FEATURE:
        (A) NAME/KEY: Peptide
        (B) LOCATION: 1..44
        (D) OTHER INFORMATION: /note= "modified human growth
            hormone release hormone"

(ix) FEATURE:
        (A) NAME/KEY: Binding-site
        (B) LOCATION: 44
        (D) OTHER INFORMATION: /note= "carboxy terminal amide"

(xi) SEQUENCE DESCRIPTION: SEQ ID NO: 10:

Tyr Ala Asp Ala Ile Phe Thr Asn Ser Tyr Arg Lys Val Leu Gly Hi
1               5                   10                  15

Leu Ser Ala Arg Lys Leu Leu His Asp Ile Met Ser Arg His His Gl
            20                  25                  30

Glu Ser Asn Gln Glu Arg Gly Ala Arg Ala Arg Leu
            35                  40
```